(12) United States Patent
Miyake

(10) Patent No.: US 11,071,523 B2
(45) Date of Patent: Jul. 27, 2021

(54) ULTRASOUND OBSERVATION DEVICE, OPERATION METHOD OF ULTRASOUND OBSERVATION DEVICE, AND COMPUTER-READABLE RECORDING MEDIUM

(71) Applicant: OLYMPUS CORPORATION, Tokyo (JP)

(72) Inventor: Tatsuya Miyake, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 473 days.

(21) Appl. No.: 16/009,719

(22) Filed: Jun. 15, 2018

(65) Prior Publication Data
US 2018/0289358 A1    Oct. 11, 2018

Related U.S. Application Data

(63) Continuation of application No. PCT/JP2016/086950, filed on Dec. 12, 2016.

(30) Foreign Application Priority Data

Dec. 18, 2015   (JP) .............................. JP2015-247567

(51) Int. Cl.
*A61B 8/00* (2006.01)
*A61B 8/12* (2006.01)
*A61B 8/08* (2006.01)

(52) U.S. Cl.
CPC .............. *A61B 8/469* (2013.01); *A61B 8/085* (2013.01); *A61B 8/12* (2013.01); *A61B 8/485* (2013.01);
(Continued)

(58) Field of Classification Search
CPC ........ G16H 168/463; A61B 8/00; A61B 8/12; A61B 8/085; A61B 8/469; A61B 8/485;
(Continued)

(56) References Cited

U.S. PATENT DOCUMENTS

| 5,615,680 A * | 4/1997 | Sano .................... A61B 8/0858 600/437 |
| 8,485,976 B2 | 7/2013 | Iimura et al. |

(Continued)

FOREIGN PATENT DOCUMENTS

| CN | 101065067 A | 10/2007 |
| CN | 102131465 A | 7/2011 |

(Continued)

OTHER PUBLICATIONS

Chinese Office Action dated Apr. 26, 2020 in Chinese Patent Application No. 201680073933.0.

(Continued)

*Primary Examiner* — Oommen Jacob
(74) *Attorney, Agent, or Firm* — Scully, Scott, Murphy & Presser, P.C.

(57) ABSTRACT

An ultrasound observation device includes a controller. The controller is configured to: generate data on an ultrasound image based on an ultrasound signal; automatically set a second region of interest that is relatively stiff in a first region of interest preset within the ultrasound image; and generate data on first and second elastic images each having a display mode according to stiffness of the corresponding first and second regions of interest.

5 Claims, 9 Drawing Sheets

(52) U.S. Cl.
CPC .............. *A61B 8/5223* (2013.01); *A61B 8/54* (2013.01); *A61B 8/463* (2013.01)

(58) Field of Classification Search
CPC ......... A61B 8/5223; A61B 8/54; A61B 8/463; A61B 8/46–469; A61B 8/488
See application file for complete search history.

(56) References Cited

U.S. PATENT DOCUMENTS

| | | | |
|---|---|---|---|
| 8,734,351 B2 | 5/2014 | Waki et al. | |
| 2002/0178833 A1* | 12/2002 | Chen | A61B 8/0833 73/795 |
| 2005/0187470 A1* | 8/2005 | Kubota | A61B 8/08 600/437 |
| 2008/0051659 A1* | 2/2008 | Waki | A61B 8/08 600/443 |
| 2008/0071174 A1* | 3/2008 | Waki | A61B 8/485 600/442 |
| 2009/0124903 A1* | 5/2009 | Osaka | A61B 8/485 600/443 |
| 2011/0152687 A1* | 6/2011 | Iimura | A61B 8/463 600/443 |
| 2011/0160588 A1* | 6/2011 | Ichikawa | A61B 8/465 600/443 |
| 2011/0255762 A1* | 10/2011 | Deischinger | A61B 8/463 382/131 |
| 2015/0190120 A1 | 7/2015 | Huang et al. | |
| 2016/0113629 A1* | 4/2016 | Miyake | A61B 8/4444 600/443 |
| 2017/0119352 A1* | 5/2017 | Anand | A61B 8/465 |

FOREIGN PATENT DOCUMENTS

| | | |
|---|---|---|
| CN | 104470443 A | 3/2015 |
| JP | 2009-261493 A | 11/2009 |
| JP | 5465671 B2 | 4/2014 |
| JP | 2015-126955 A | 7/2015 |
| JP | 5820962 B1 | 11/2015 |
| WO | WO 2006/013916 A1 | 2/2006 |

OTHER PUBLICATIONS

Extended Supplementary European Search Report dated Jul. 1, 2019 in European Patent Application No. 16 87 5604.7.
International Search Report dated Feb. 7, 2017 issued in PCT/JP2016/086950.

* cited by examiner

ULTRASOUND OBSERVATION DEVICE, OPERATION METHOD OF ULTRASOUND OBSERVATION DEVICE, AND COMPUTER-READABLE RECORDING MEDIUM

CROSS REFERENCES TO RELATED APPLICATIONS

This application is a continuation of PCT international application Ser. No. PCT/JP2016/086950 filed on Dec. 12, 2016 which designates the United States, incorporated herein by reference, and which claims the benefit of priority from Japanese Patent Applications No. 2015-247567, filed on Dec. 18, 2015, incorporated herein by reference.

BACKGROUND

1. Technical Field

The present disclosure relates to an ultrasound observation device that observes tissue of an observation target using ultrasound, an operation method of the ultrasound observation device, and a computer-readable recording medium.

2. Related Art

In the related art, ultrasound elastography is known as a technique for diagnosing an observation target using ultrasound (for example, see Japanese Patent No. 5465671). The ultrasound elastography is a technique that utilizes the fact that the stiffness of cancer and tumor tissue in a living body varies according to advancement of disease and the living body. In this technique, an elastic image in which information on the stiffness of biological tissue is formed into an image is generated, by adding colors on the basis of an average value of the displacement amount of the biological tissue in a predetermined region of interest (ROI).

SUMMARY

In some embodiments, an ultrasound observation device includes a controller. The controller is configured to: generate data on an ultrasound image based on an ultrasound signal; automatically set a second region of interest that is relatively stiff in a first region of interest preset within the ultrasound image; and generate data on first and second elastic images each having a display mode according to stiffness of the corresponding first and second regions of interest.

In some embodiments, provided is an operation method of an ultrasound observation device. The operation method includes: generating, by a controller, data on a first elastic image having a display mode according to stiffness of a first region of interest preset within an ultrasound image that is generated based on an ultrasound signal; setting, by the controller, a second region of interest that is relatively stiff in the first region of interest; and generating, by the controller, data on a second elastic image having a display mode according to stiffness of the second region of interest.

In some embodiments, provided is a non-transitory computer-readable recording medium with an executable program stored thereon. The program is a program operating an ultrasound observation device. The program causes the ultrasound observation device to execute: generating, by a controller, data on a first elastic image having a display mode according to stiffness of a first region of interest preset within an ultrasound image that is generated based on an ultrasound signal; setting, by the controller, a second region of interest that is relatively stiff in the first region of interest; and generating, by the controller, data on a second elastic image having a display mode according to stiffness of the second region of interest.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, modes for carrying out the disclosure (hereinafter, referred to as "embodiments") will be described in detail with reference to the accompanying drawings.

FIRST EMBODIMENT

Figure 1:
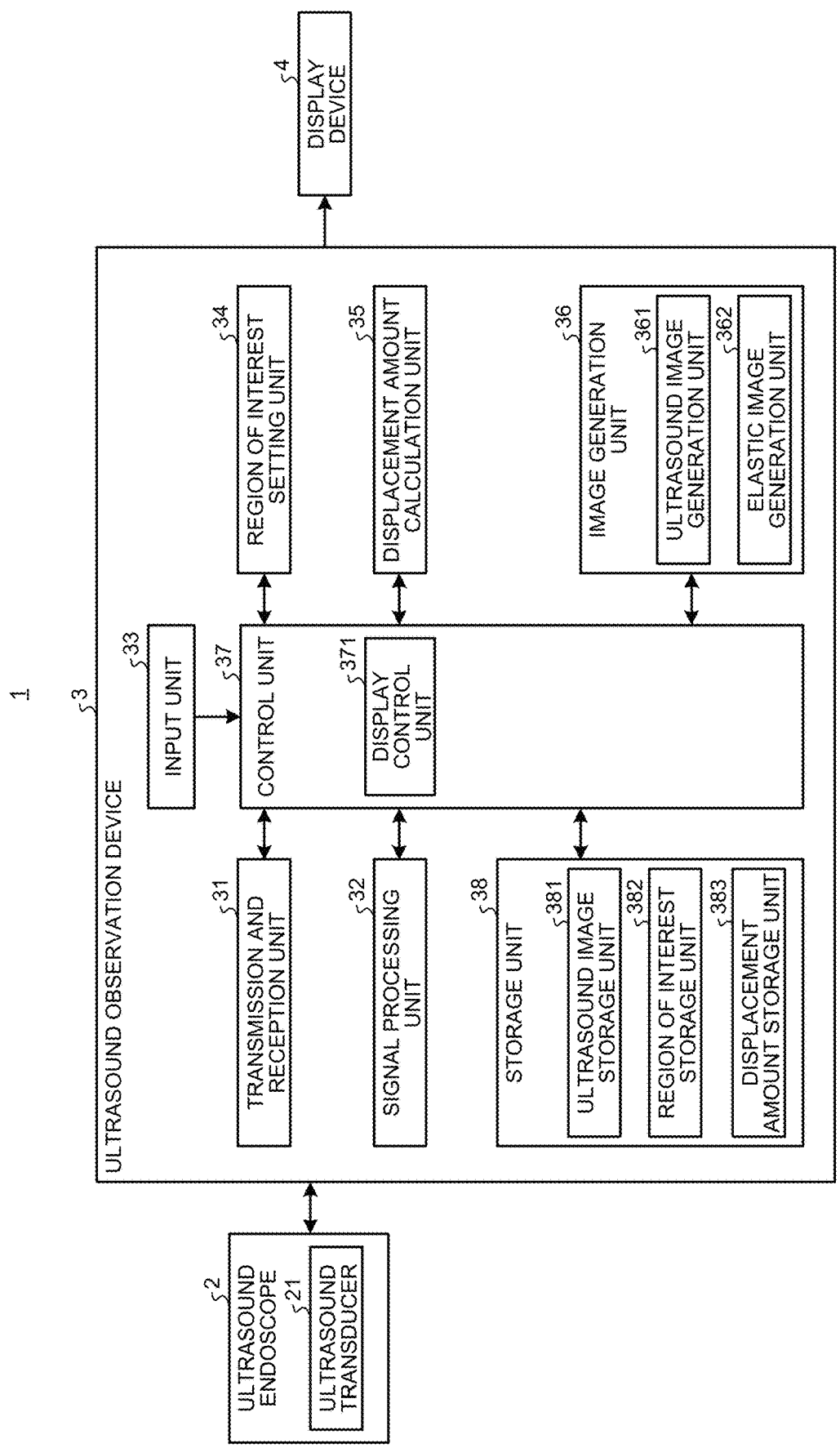
FIG. 1 is a schematic diagram of a configuration of an ultrasound diagnostic system provided with an ultrasound observation device according to a first embodiment of the disclosure.

FIG. 1 is a schematic diagram of a configuration of an ultrasound diagnostic system provided with an ultrasound observation device according to a first embodiment of the disclosure. An ultrasound diagnostic system 1 illustrated in FIG. 1 includes an ultrasound endoscope 2, an ultrasound observation device 3, and a display device 4.

The ultrasound endoscope 2 includes an ultrasound transducer 21 that is provided at the distal end of the ultrasound endoscope 2, transmits ultrasound to the subject that is the observation target, and receives the ultrasound reflected by the subject. The ultrasound transducer 21 converts an electric pulse signal received from the ultrasound observation device 3 to an ultrasonic pulse (acoustic pulse), and emits the ultrasonic pulse to the subject. The ultrasound transducer 21 also converts an ultrasound echo reflected by the subject to an electric echo signal (ultrasound signal) to output. The ultrasound transducer 21 may be an electron scanning type or a mechanical scanning type. For example, various types of the ultrasound endoscopes 2 are known depending on the observation target such as digestive canals (esophagus, stomach, duodenum, and large intestine) and respiratory organs (trachea and bronchi) of the subject.

The ultrasound endoscope 2 may also include an imaging unit that captures an image inside the subject, and a light guide that guides illumination light from a light source device for generating illumination light emitted to the subject to the distal end of the ultrasound endoscope 2 when the image is captured.

The ultrasound observation device 3 receives and transmits electric signals from and to the ultrasound endoscope 2 via an ultrasound cable. The ultrasound observation device 3 generates an ultrasound image and the like by performing a predetermined process on an electric echo signal received from the ultrasound endoscope 2. The ultrasound observation device 3 includes a transmission and reception unit 31, a signal processing unit 32, an input unit 33, a region of interest setting unit 34, a displacement amount calculation unit 35, an image generation unit 36, a control unit 37, and a storage unit 38. The transmission and reception unit 31 transmits and receives signals to and from the ultrasound transducer 21. The signal processing unit 32 generates digital reception data on the basis of the echo signal received from the transmission and reception unit 31. The input unit 33 receives an input of various types of information including an operation instruction signal of the ultrasound observation device 3. The region of interest setting unit 34 sets a region of interest within an ultrasound image. The displacement amount calculation unit 35 calculates a displacement amount between images at an observation point (sampling point) within the region of interest. The image generation unit 36 generates data on various types of images including an ultrasound image and an elastic image. The control unit 37 integrally controls the entire operation of the ultrasound diagnostic system 1. The storage unit 38 stores therein various types of information required for operating the ultrasound observation device 3. The ultrasound observation device 3 can set an elastography mode that expresses information on relative stiffness of the observation target in a region of interest by forming an image of the information using visual information such as colors.

The transmission and reception unit 31 transmits pulse-like transmission drive wave signals to the ultrasound transducer 21 on the basis of a predetermined waveform and transmission timing. The transmission and reception unit 31 also receives an electric echo signal from the ultrasound transducer 21. The transmission and reception unit 31 has a function of transmitting various types of control signals output from the control unit 37 to the ultrasound endoscope 2, receiving various types of information including an identification ID from the ultrasound endoscope 2, and transmitting the various types of information to the control unit 37.

The signal processing unit 32 performs a known process such as bandpass filtering, envelope-detection, and logarithmic conversion on an echo signal, and generates digital reception data for an ultrasound image (hereinafter, referred to as reception data). The signal processing unit 32 is implemented by using a general processor such as a central processing unit (CPU), a dedicated integrated circuit that executes a specific function such as an application specific integrated circuit (ASIC) or a field programmable gate array (FPGA), or the like.

The input unit 33 receives an input of a signal instructing to set a first region of interest (hereinafter, referred to as a first ROI). The input unit 33 is configured using a user interface such as a keyboard, a mouse, and a touch panel.

The region of interest setting unit 34 sets the first ROI on the basis of the setting input received by the input unit 33. Moreover, the region of interest setting unit 34 sets a region relatively stiff within the first ROI as a second region of interest (hereinafter, referred to as a second ROI), on the basis of the calculation result of the displacement amount calculation unit 35, which will be described below.

The displacement amount calculation unit 35 calculates the displacement amount of tissue at the observation point (sampling point) within the region of interest according to the pressure applied to the subject by the heartbeat, on the basis of data on the ultrasound image generated by an ultrasound image generation unit 361 of the image generation unit 36, which will be described below. For example, the displacement amount calculation unit 35 calculates the displacement amount by comparing the latest ultrasound image with the ultrasound image generated in the preceding frame.

The image generation unit 36 includes the ultrasound image generation unit 361 and an elastic image generation unit 362. The ultrasound image generation unit 361 generates data on the ultrasound image on the basis of reception data. The elastic image generation unit 362 generates an elastic image that visually expresses information on the stiffness of tissue of the observation target on the basis of the displacement amount within the region of interest.

For example, the data on the ultrasound image generated by the ultrasound image generation unit 361 is B-mode image data in which the amplitude is converted to luminance.

The elastic image generation unit 362 generates data on first and second elastic images that each have a display mode according to the stiffness of the corresponding first and second regions of interest. The elastic image generated by the elastic image generation unit 362 is an image obtained by applying visual information such as color and pattern on each point within the region of interest on the basis of the calculation result of the displacement amount calculation unit 35. More specifically, the elastic image generation unit 362 generates data on an elastic image by applying green to the tissue corresponding to the average stiffness within the region of interest, bluish color to the tissue stiffer than the average, and reddish color to the tissue softer than the average.

The control unit 37 includes a display control unit 371 that controls display performed by the display device 4. The display control unit 371 controls the display device 4 so as to display various types of images generated by the image generation unit 36.

The control unit 37 is implemented by using a general processor such as the CPU having calculation and control functions, or a dedicated integrated circuit such as the ASIC or the FPGA. When the control unit 37 is implemented by the general processor or the FPGA, the control unit 37 integrally controls the ultrasound observation device 3 by reading out various computer programs and various types of data stored in the storage unit 38 from the storage unit 38, and executing various arithmetic processes relating to the operation of the ultrasound observation device 3. When the control unit 37 is configured using the ASIC, the control unit 37 may execute various processes independently, or may execute the various processes by using the various types of data stored in the storage unit 38. In the present first embodiment, the control unit 37 and at least a part of the signal processing unit 32, the region of interest setting unit 34, the displacement amount calculation unit 35, and the image generation unit 36 may be configured using a common general processor, a dedicated integrated circuit, or the like.

The storage unit 38 includes an ultrasound image storage unit 381, a region of interest storage unit 382, and a displacement amount storage unit 383. The ultrasound image storage unit 381 temporarily stores therein at least data on a plurality of the ultrasound images generated by the ultrasound image generation unit 361. The region of interest storage unit 382 stores therein information on the first ROI set for the ultrasound image. The displacement amount storage unit 383 stores therein the displacement amount calculated by the displacement amount calculation unit 35. The number of pieces of ultrasound images to be stored in the ultrasound image storage unit 381 is set in advance. The displacement amount storage unit 383 stores therein data on the displacement amount as much as the displacement amount calculation unit 35 requires for calculating the displacement amount.

The storage unit 38 stores therein various computer programs including an operation program for executing the operation method of the ultrasound observation device 3. The various computer programs including the operation program may be stored in a computer readable medium such as a hard disk, a flash memory, a compact disc-read only memory (CD-ROM), a digital versatile disc-read only memory (DVD-ROM) and a flexible disk to be distributed widely. The various computer programs described above may also be obtained by downloading via a communication network. For example, the communication network described above is implemented by the existing public network, a local area network (LAN), a wide area network (WAN), and the like, and may be either wired or wireless.

The storage unit 38 is implemented by a read only memory (ROM) in which various computer programs and the like are installed in advance, a random access memory (RAM) that stores therein operation parameter and data of various processes, and the like.

The display device 4 is constituted of liquid crystal, organic electro luminescence (EL), or the like. The display device 4 receives image data such as an ultrasound image and an elastic image generated by the ultrasound observation device 3, and displays the images.

Figure 2:
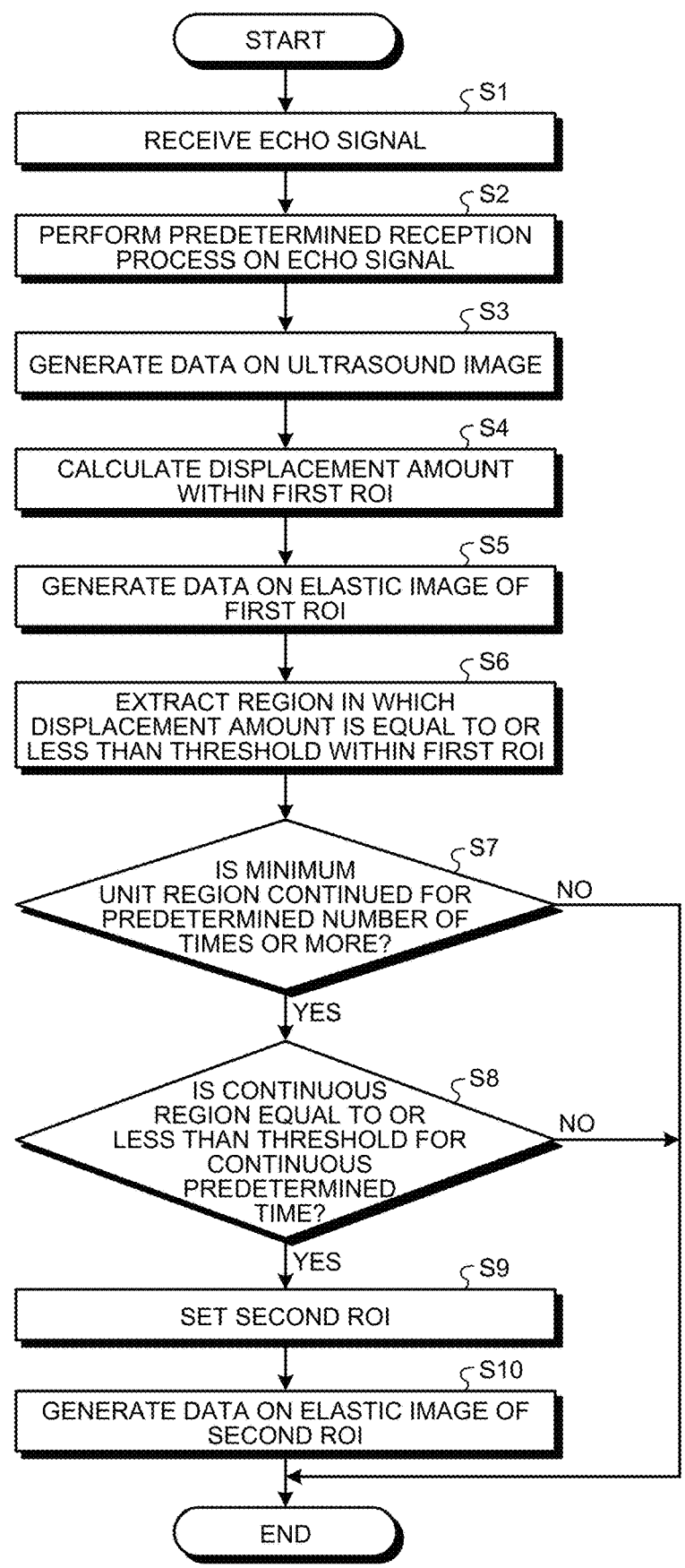
FIG. 2 is a flowchart illustrating the outline of processing performed by the ultrasound observation device according to the first embodiment of the disclosure.

FIG. 2 is a flowchart illustrating the outline of processing performed by the ultrasound observation device 3. The flowchart illustrated in FIG. 2 is a process in which the ultrasound diagnostic system 1 is set to the elastography mode, and the setting of the first ROI in the ultrasound image is completed after the transmission and reception unit 31 starts transmitting transmission drive wave signals, and the ultrasound transducer 21 starts transmitting ultrasound.

First, the transmission and reception unit 31 receives an echo signal that is the measurement result of the observation target by the ultrasound transducer 21 from the ultrasound endoscope 2 (step S1).

Next, the signal processing unit 32 generates reception data by performing a predetermined reception process on the echo signal received from the ultrasound transducer 21 (step S2). More specifically, the transmission and reception unit 31 performs a process such as filtering and analog-to-digital (AD) conversion, after amplifying (sensitivity time control (STC) correcting) the echo signal.

The ultrasound image generation unit 361 then generates data on the ultrasound image using the reception data generated by the signal processing unit 32, stores the generated data in the ultrasound image storage unit 381, and outputs the data to the display device 4 under the control of the display control unit 371 (step S3).

Subsequently, the displacement amount calculation unit 35 calculates the displacement amount at the observation point within the first ROI stored in the region of interest storage unit 382 (step S4). In this process, the displacement amount calculation unit 35 calculates the displacement amount at each observation point, by using the latest data on the ultrasound image and the past data on the ultrasound image stored in the ultrasound image storage unit 381.

Figure 3:
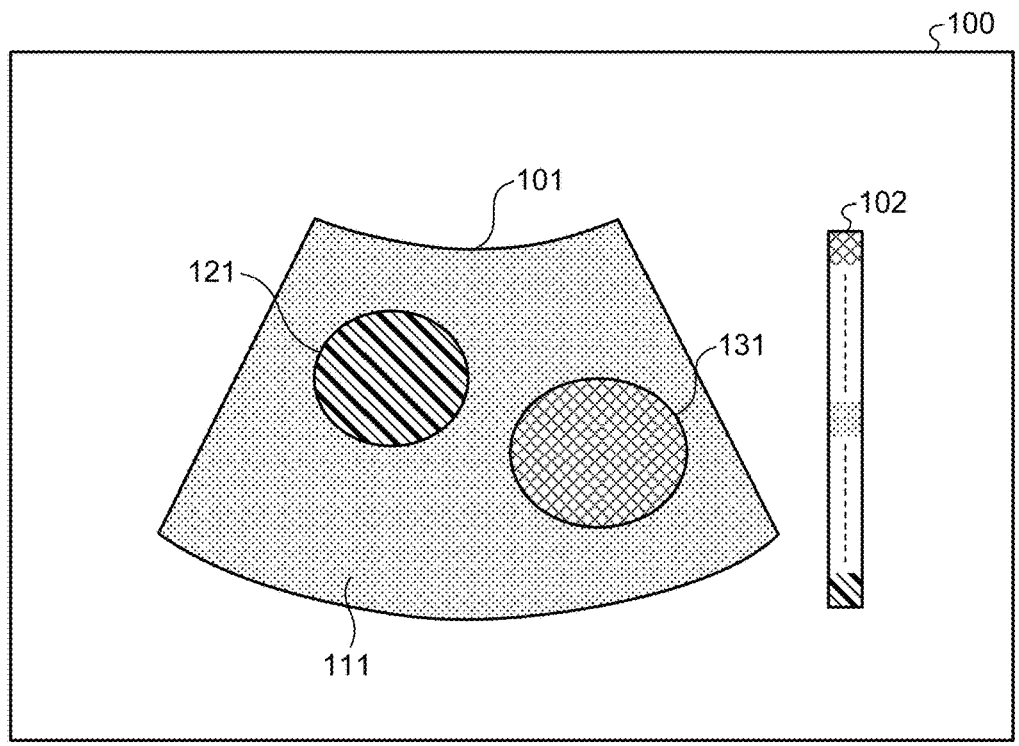
FIG. 3 is a diagram illustrating a display example of an elastic image of a first region of interest on a display device.

The elastic image generation unit 362 then generates data on the elastic image of the first ROI (first elastic image) using the calculation result of the displacement amount at each observation point at step S4, and outputs the data to the display device 4 (step S5). FIG. 3 is a diagram illustrating a display example of an elastic image of the first ROI on the display device 4. An elastic image 100 illustrated in FIG. 3 is displayed as an image in which the stiffness of each tissue inside a first ROI 101 is identifiable by color. In FIG. 3, the differences in colors are schematically expressed by patterns. A color scale 102 indicating the colors to be used in the elastic image 100 is displayed at the right side of the first ROI 101. For example, the tissue becomes stiffer in descending order from top to bottom in the color scale 102. In FIG. 3, only a part of the color scale 102 is schematically illustrated. The displacement amount of a region 111 in FIG. 3 is average. Alternatively, a region 121 is a softest region, and a region 131 is a stiffest region. The display device 4 displays a B mode image and the elastic image 100 side by side. The display device 4 may also display the elastic image 100 on the B mode image in an overlapping manner. In this case, the image generation unit 36 generates data on an image in which the elastic image 100 is overlapped with the B mode image, and outputs the data on the image to the display device 4 under the control of the display control unit 371.

Subsequently, the region of interest setting unit 34 extracts a region in which the displacement amount is equal to or less than a threshold within the first ROI (step S6). For example, the threshold in this case is set as a value the displacement amount of which is smaller than a reference value as much as a predetermined amount, on the basis of the average of the displacement amount within the first ROI. Moreover, the threshold may be the average value of the displacement amount within the first ROI. The reference value may also be a statistical amount such as the center value or the most frequent value of the displacement amount within the first ROI.

Then, the region of interest setting unit 34 determines whether the minimum unit region (pixel or block) is continued for a predetermined number of times or more in the extracted region (step S7). In this example, for example, the predetermined number of times is the number corresponding to the size that a user can view the continuous region on the screen. As a result of determination, when the minimum unit region is continued for a predetermined number of times or more (Yes at step S7), the region of interest setting unit 34 determines whether the continuous region is continuously equal to or less than the threshold for a predetermined time, by referring to a plurality of the past displacement amounts stored in the displacement amount storage unit 383 (step S8). As a result of determination, when the continuous region is continuously equal to or less than the threshold for a predetermined time (Yes at step S8), the region of interest setting unit 34 sets the region as the second ROI (step S9). In this example, for example, the predetermined time is about the same time as the heartbeat cycle of the subject.

Figure 4:
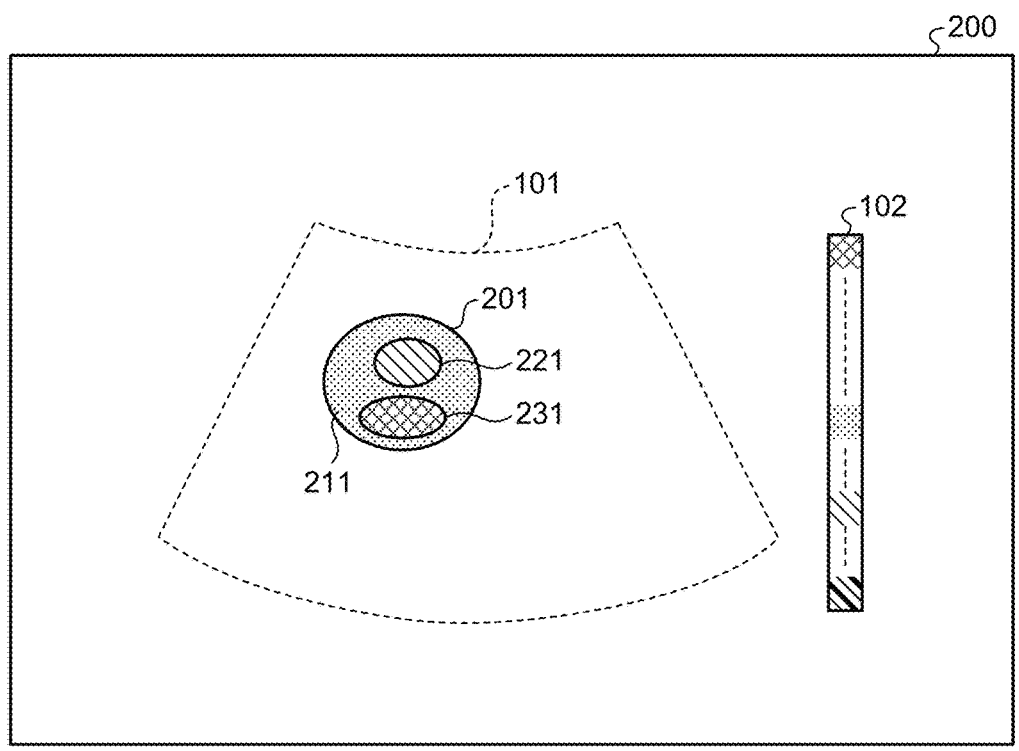
FIG. 4 is a diagram illustrating a display example of an elastic image of a second region of interest on the display device.

After step S9, the elastic image generation unit 362 generates data on an elastic image of the second ROI (second elastic image), and outputs the data to the display device 4 under the control of the display control unit 371 (step S10). FIG. 4 is a diagram illustrating a display example of an elastic image of the second ROI on the display device 4. An elastic image 200 illustrated in FIG. 4 is displayed as an image in which the stiffness of each tissue inside a second ROI 201 is identifiable by color. Similar to FIG. 3, in FIG. 4 also, the differences in colors are schematically expressed by patterns. The displacement amount of a region 211 in the elastic image 200 is average. Alternatively, a region 221 is a relatively soft region, and a region 231 is a stiffest region. The display device displays the elastic image 200 and the elastic image 100 side by side. Similar to the elastic image 100, the display device 4 may also display the elastic image 200 on the B mode image in an overlapping manner. In this case, the image generation unit 36 generates data on an image in which the elastic image 200 is overlapped with the B mode image, and outputs the data on the image to the display device 4 under the control of the display control unit 371. After step S10, the ultrasound observation device 3 finishes the series of processes.

When the minimum unit region is not continued for a predetermined number of times or more at step S7 (No at step S7), or when the continuous region is not continuously equal to or less than the threshold for a predetermined time at step S8 (No at step S8), the ultrasound observation device 3 finishes the series of processes.

While being set to the elastography mode, the ultrasound observation device 3 performs the processes from step S1 to step S10 every time an echo signal is received.

The first embodiment of the disclosure as described above can eliminate the need of setting the second ROI, because the second ROI that is relatively stiff within the first ROI is automatically set while the elastic image of the first ROI is displayed in real time, and the elastic image of the second ROI is generated. Consequently, it is possible to easily perform both observations on screening and careful examination in the ultrasound elastography without taking trouble.

With the present first embodiment, when a region in which the displacement amount is smaller than the threshold within the first ROI is spatially continued, and the continuous region is continued for a predetermined time, the region is set as the second ROI. Consequently, it is possible to accurately set a region in which the displacement amount does not change continuously over a plurality of frames (region where the displacement amount is not changed over time) as the second ROI, even when the ultrasound elastography is performed by using the heartbeat of a living body that is the observation target, as the ultrasound endoscope.

Modification 1-1

Figure 5:
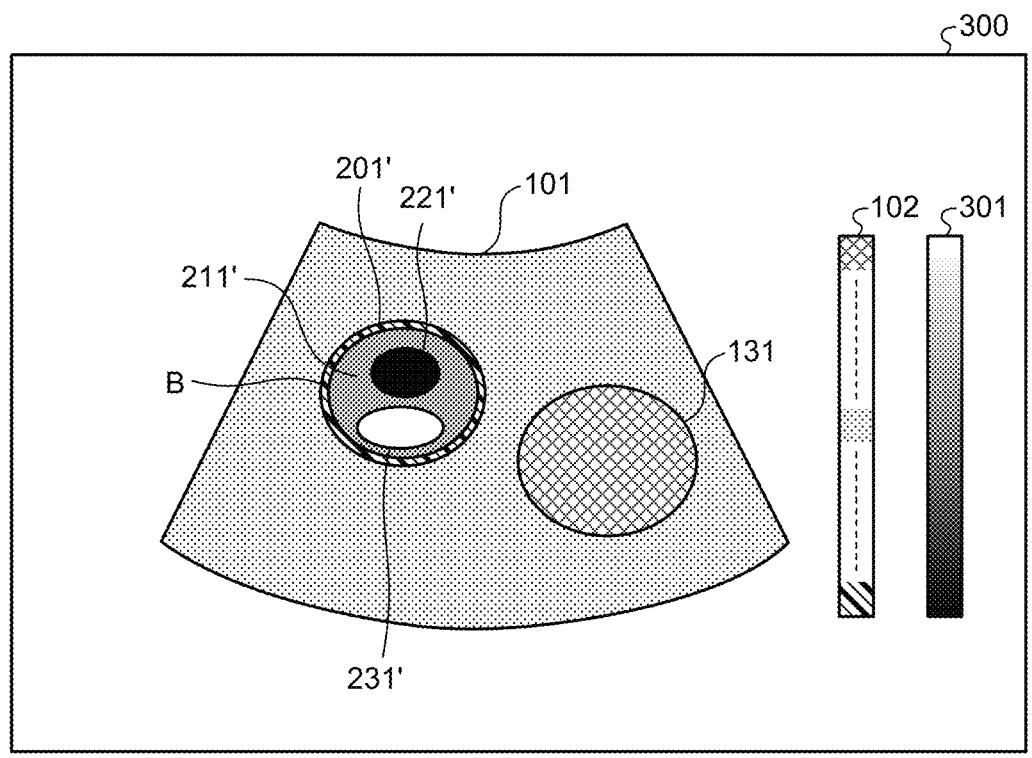
FIG. 5 is a diagram illustrating a display example of an elastic image of the second ROI on the display device generated by an ultrasound observation device according to a modification 1-1 of the first embodiment of the disclosure.

FIG. 5 is a diagram illustrating a display example of an elastic image of the second ROI on the display device 4 generated by an ultrasound observation device according to a modification 1-1 of the present first embodiment. In an elastic image 300 illustrated in FIG. 5, a region excluding a second ROI 201' from the first ROI 101 and the second ROI 201' corresponding to the excluded region are displayed in a single image in different color scales. Consequently, in the elastic image 300, a color scale 301 of the elastic image of the second ROI 201' in addition to the color scale 102 of the elastic image of the first ROI 101 are displayed side by side. For comparison convenience, the elastic image 300 in FIG. 5 is assumed to observe the same tissue as that of the corresponding elastic images 100 and 200 illustrated in FIG. 3 and FIG. 4. Consequently, regions 211', 221', 231' respectively correspond to the regions 211, 221, and 231 illustrated in FIG. 4.

In the elastic image 300, the same color as that of the region 121 in FIG. 3 is applied to a boundary portion B between the second ROI 201' and the first ROI 101 on the basis of the color scale 102 of the first ROI 101. In this manner, by displaying the first ROI 101 and the second ROI 201' in an identifiable display mode, the user can easily identify the boundary between the first ROI 101 and the second ROI 201'. In the present modification 1-1, at least the color scales of the first ROI 101 and the second ROI 201' may be different, and the boundary portion B may not be displayed.

Modification 1-2

Figure 6:
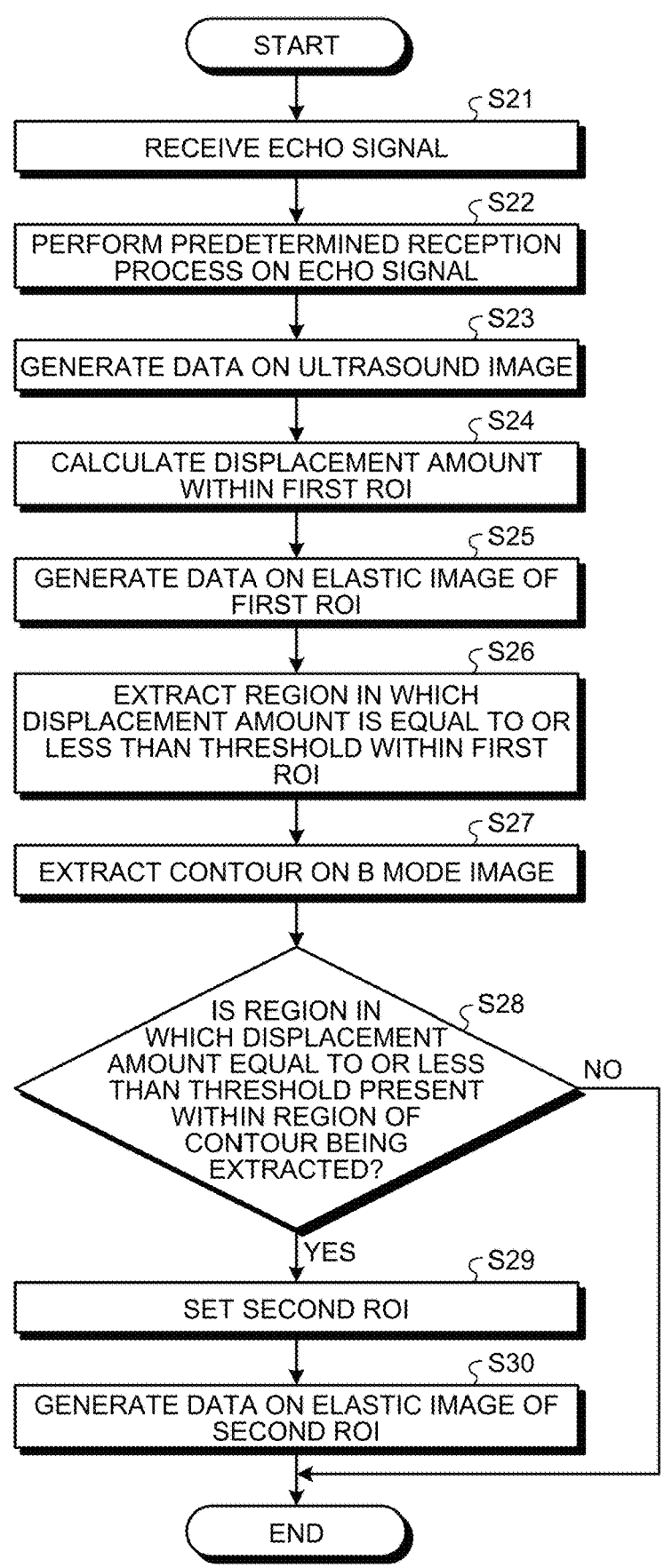
FIG. 6 is a flowchart illustrating the outline of processing performed by an ultrasound observation device according to a modification 1-2 of the first embodiment of the disclosure.

FIG. 6 is a flowchart illustrating the outline of processing performed by an ultrasound observation device according to a modification 1-2 of the present first embodiment. The flowchart illustrated in FIG. 6 is also a process in which the ultrasound diagnostic system 1 is set to the elastography mode, and the setting of the first ROI in the ultrasound image is completed, after the transmission and reception unit 31 starts transmitting transmission drive wave signals, and the ultrasound transducer 21 starts transmitting ultrasound. Processes from step S21 to step S26 sequentially correspond to the processes from step S1 to step S6 described in the first embodiment.

At step S27, the region of interest setting unit 34 performs a contour extraction (edge extraction) process on the B mode image (step S27). For example, the region of interest setting unit 34 extracts contour by applying a known filter such as Sobel or Laplacian.

When a region in which the displacement amount is equal to or less than a threshold is present within the region of the contour that is extracted (Yes at step S28), the region of interest setting unit 34 sets a closed region bounded by the outline as the second ROI (step S29). In this example also, based on the average value of the displacement amount within the first ROI, the threshold is set as a value the displacement amount of which is smaller than the reference value as much as a predetermined amount.

Then, the elastic image generation unit 362 generates data on the elastic image of the second ROI, and outputs the data to the display device 4 (step S30).

At step S28, when a region in which the displacement amount is equal to or less than a threshold is not present within the region of the contour that is extracted (No at step S28), the ultrasound observation device 3 finishes the series of processes.

With the present modification 1-2 described above, it is possible to accurately set the relatively stiff region as the second ROI, because the contour of the observation target on the ultrasound image is extracted, and the closed region bounded by the extracted contour is set as the second region of interest, among the regions in which the displacement amount at each observation point within the first region of interest is smaller than a predetermined threshold.

SECOND EMBODIMENT

Figure 7:
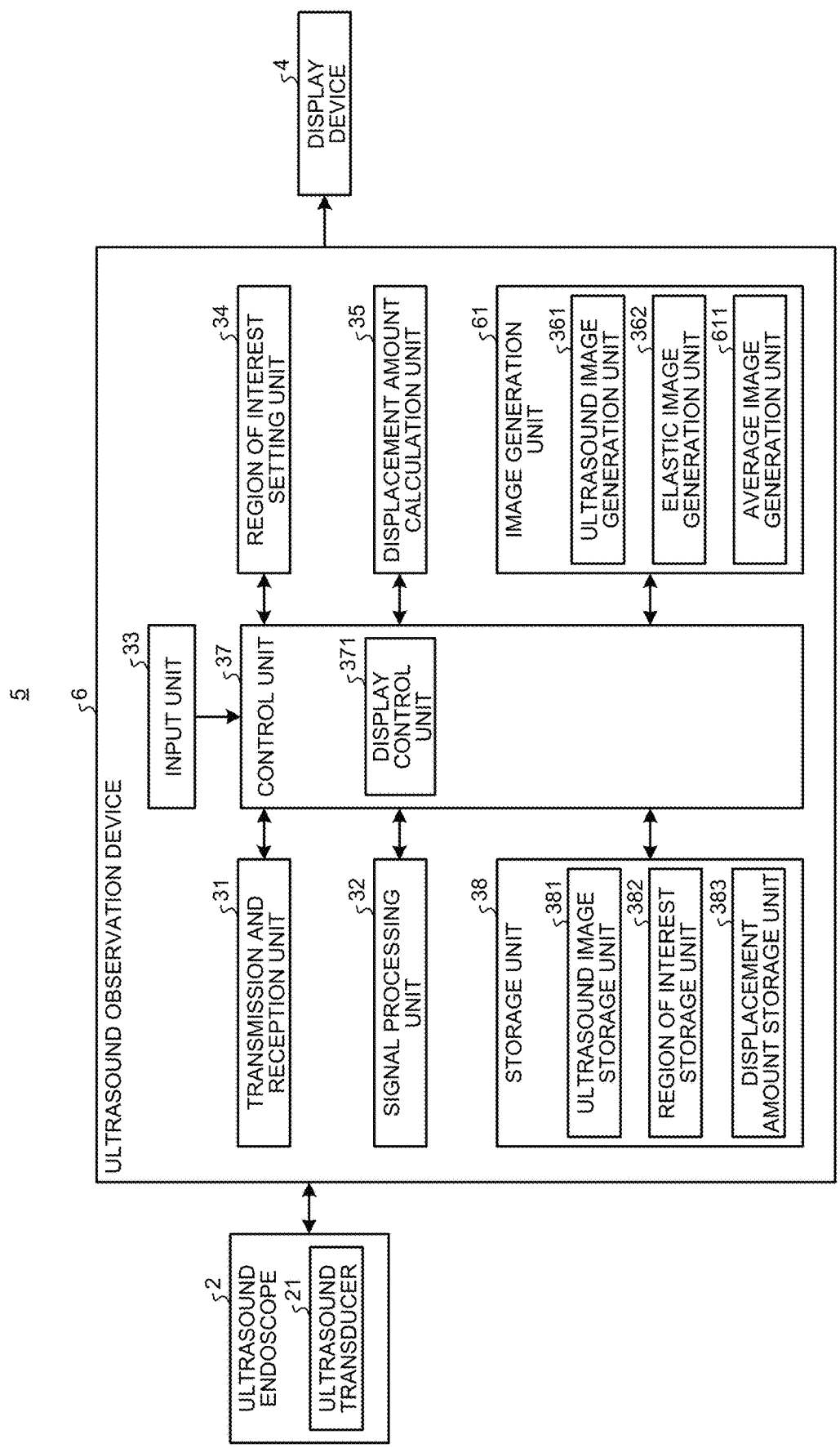
FIG. 7 is a schematic diagram of a configuration of an ultrasound diagnostic system provided with an ultrasound observation device according to a second embodiment of the disclosure.

FIG. 7 is a schematic diagram of a configuration of an ultrasound diagnostic system provided with an ultrasound observation device according to a second embodiment of the disclosure. An ultrasound diagnostic system 5 illustrated in FIG. 7 includes the ultrasound endoscope 2, an ultrasound observation device 6, and the display device 4. The configuration of the ultrasound diagnostic system 5 other than the ultrasound observation device 6 is the same as that of the ultrasound diagnostic system 1 described in the first embodiment.

The configuration of an image generation unit in the ultrasound observation device 6 is different from that in the ultrasound observation device 3 described in the first embodiment. An image generation unit 61 provided in the ultrasound observation device 6 includes an average image generation unit 611 in addition to the ultrasound image generation unit 361 and the elastic image generation unit 362.

When a freeze instruction signal that makes the display on the display device 4 into a still image is input from the input unit 33, and when an average instruction signal is further input from the input unit 33, the average image generation unit 611 generates data on the average image by adding and averaging pixel values of pixels of a plurality of the ultrasound images that are formed of the ultrasound images specified by the average instruction signal. The input unit 33 receives an input of selecting the images to be added and averaged. More specifically, when the input unit 33 receives an input of an average instruction signal, the display control unit 371 causes the display device 4 to display the past ultrasound image to be added and averaged. In this process, the display control unit 371 may cause the display device 4 to display a single ultrasound image at a time, or may cause the display device 4 to display several pieces of ultrasound images at a time. The average image generation unit 611 generates data on the average image using the ultrasound images selected from the ultrasound images displayed on the display device 4.

The region of interest setting unit 34 sets the second ROI relative to the average image, on the basis of the data on the average image generated by the average image generation unit 611. The elastic image generation unit 362 automatically generates data on the elastic image of the second ROI in the average image.

Figure 8:
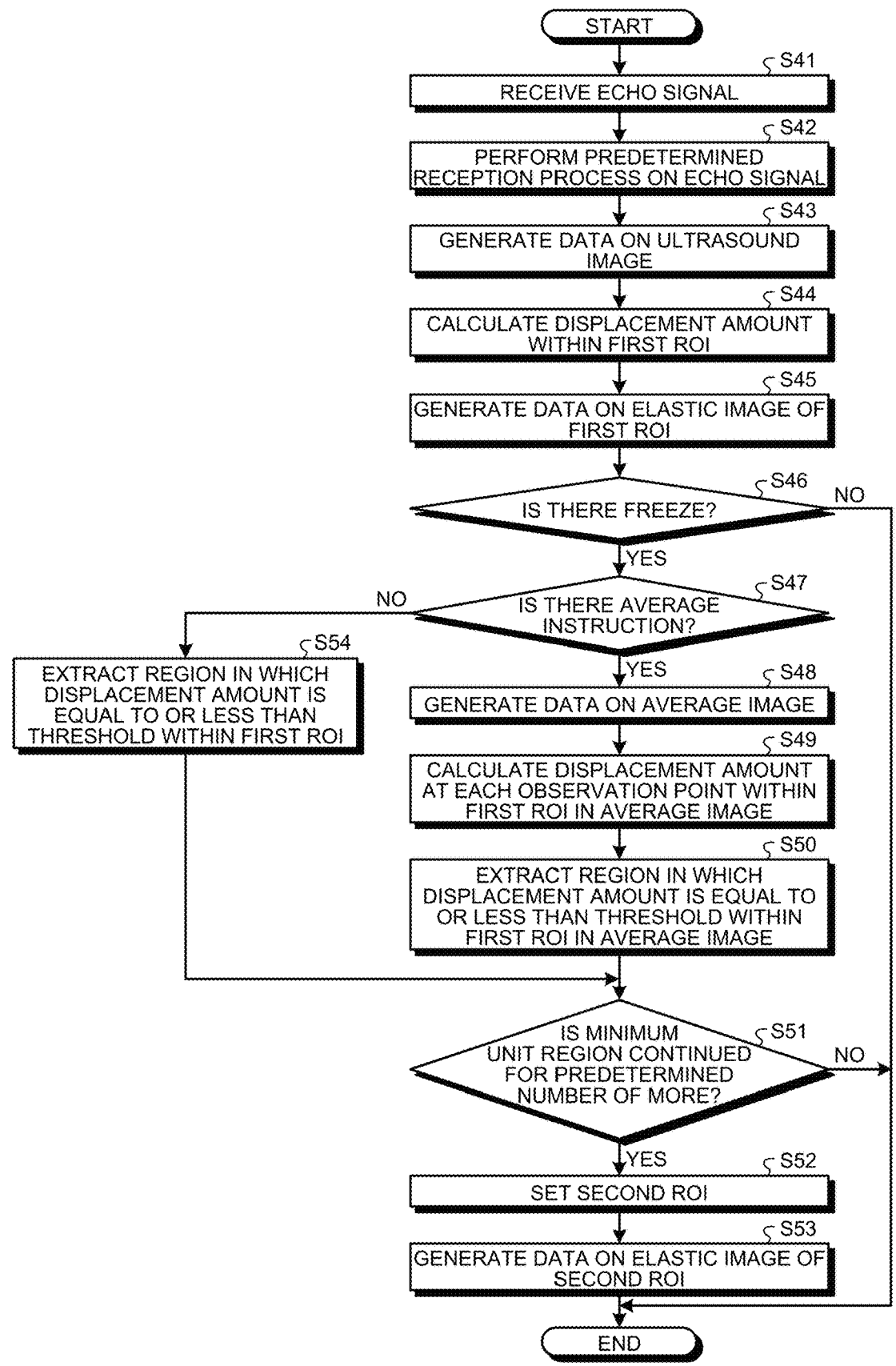
FIG. 8 is a flowchart illustrating the outline of processing performed by the ultrasound observation device according to the second embodiment of the disclosure.

FIG. 8 is a flowchart illustrating the outline of processing performed by the ultrasound observation device 6. The flowchart illustrated in FIG. 8 is also a process in which the ultrasound diagnostic system 5 is set to the elastography mode, and the setting of the first ROI in the ultrasound image is completed after the transmission and reception unit 31 starts transmitting transmission drive wave signals, and the ultrasound transducer 21 starts transmitting ultrasound. Processes from step S41 to step S45 sequentially correspond to the processes from step S1 to step S5 described in the first embodiment.

After step S45, when the input unit 33 receives an input of a freeze instruction signal (Yes at step S46), the process proceeds to step S47. Alternatively, after step S45, when the input unit 33 does not receive the freeze instruction signal (No at step S46), the ultrasound observation device 6 finishes the series of processes.

At step S47, when the input unit 33 receives an input of the average instruction signal (Yes at step S47), the image generation unit 36 generates data on the average image by adding and averaging the pixel values of the pixels of the ultrasound images that are formed of the ultrasound images specified by the average instruction signal (step S48).

The displacement amount calculation unit 35 then calculates the displacement amount at each observation point within the first ROI in the average image (step S49). The displacement amount calculation unit 35 reads out the displacement amount at each observation point in the ultrasound images that form the average image from the displacement amount storage unit 383, and calculates the average of the displacement amount at each observation point. The average will be the displacement amount at each observation point of the average image.

Subsequently, the region of interest setting unit 34 extracts a region in which the displacement amount is equal to or less than a threshold within the first ROI in the average image (step S50). This threshold is set as a value the displacement amount of which is smaller than a reference value as much as the predetermined amount, assuming that the average obtained when the displacement amount at each observation point within the first ROI in the average image is population is the reference value. The reference value may also be the threshold. The statistical amount such as the center value or the most frequent value may be applied as the reference value, instead of the average.

The region of interest setting unit 34 then determines whether the minimum unit region (pixel or block) in the extracted region is continued for a predetermined number of times or more (step S51). The predetermined number is the same as the number described at step S7 in the first embodiment. When determination reveals that the minimum unit region in the extracted region is continued for a predetermined number of times or more (Yes at step S51), the region of interest setting unit 34 sets the region as the second ROI (step S52). On the other hand, when the minimum unit region in the extracted region is not continued for a predetermined number of times or more (No at step S51), the ultrasound observation device 6 finishes the series of processes.

After step S52, the elastic image generation unit 362 generates data on an elastic image of the second ROI (second elastic image) set in the average image, and outputs the data to the display device 4 under the control of the display control unit 371 (step S53). After step S53, the ultrasound observation device 6 finishes the series of processes. The display device 4 displays the average image and the elastic image of the second ROI side by side. The display device 4 may also display the average image and the elastic image of the second ROI in an overlapping manner.

The following describes a case when the input unit 33 does not receive the average instruction signal at step S47 (No at step S47). In this case, the region of interest setting unit 34 extracts a region in which the displacement amount is equal to or less than a threshold within the first ROI (step S54). The threshold in this process is the same as the threshold at step S6 described in the first embodiment. The ultrasound observation device 6 then proceeds the process to step S51.

The elastic image generation unit 362 may also generate data on the elastic image of the first ROI in the average image and output the data to the display device 4. In this case, the display device 4 displays the average image and the elastic images of the first and second ROI.

The second embodiment of the disclosure described above can eliminates the need of setting the second ROI, because the freeze operation is performed while the elastic image of the first ROI is displayed, the data on the average image of a predetermined number of ultrasound images is generated when the average instruction operation is performed, the relatively stiff second ROI is automatically set within the first ROI in the average image, and the elastic image relative to the second ROI is generated. Consequently, it is possible to easily perform both observations on screening and careful examination in the ultrasound elastography without taking trouble.

Moreover, with the present second embodiment, when a region in which the displacement amount is smaller than the threshold within the first ROI is spatially continued, the region is set as the second ROI. Consequently, it is possible to accurately set the second ROI as the region in which the displacement amount does not change continuously over a plurality of frames, even when the ultrasound elastography is performed by using the heartbeat of a living body that is the observation target, as the ultrasound endoscope.

Modification 2-1

Figure 9:
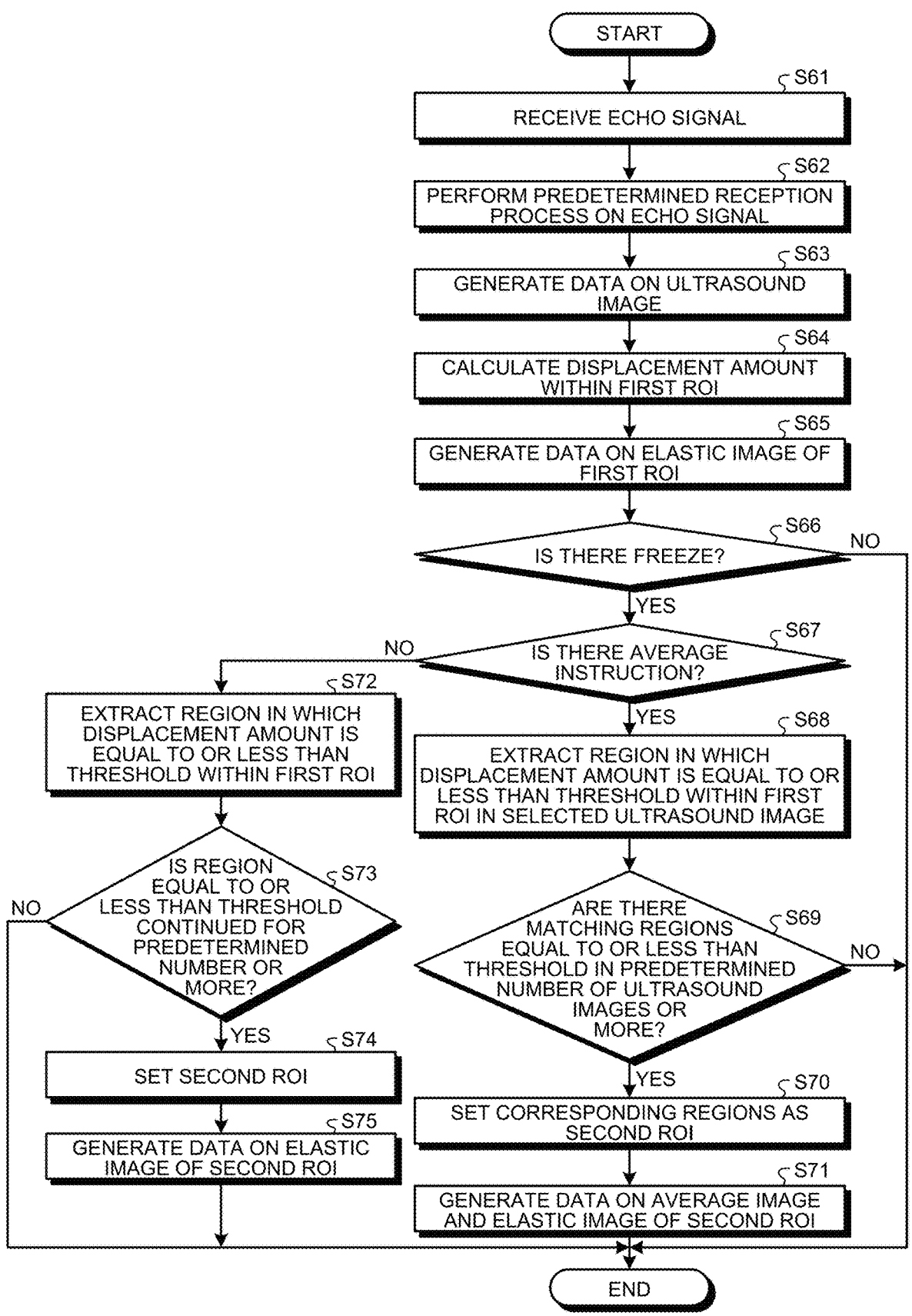
FIG. 9 is a flowchart illustrating the outline of processing performed by an ultrasound observation device according to a modification 2-1 in the second embodiment of the disclosure.

FIG. 9 is a flowchart illustrating the outline of processing performed by an ultrasound observation device according to a modification 2-1 in the present second embodiment. The flowchart illustrated in FIG. 9 is also a process in which the ultrasound diagnostic system 5 is set to the elastography mode, and the setting of the first ROI in the ultrasound image is completed after the transmission and reception unit 31 starts transmitting transmission drive wave signals, and the ultrasound transducer 21 starts transmitting ultrasound. Processes from step S61 to step S67 sequentially correspond to the processes from step S41 to step S47 described in the second embodiment.

At step S67, when the input unit 33 receives an input of an average instruction signal (Yes at step S67), the region of interest setting unit 34 refers to the displacement amount storage unit 383, and extracts the region in which the displacement amount is equal to or less than a threshold within the first ROI in the selected ultrasound image (step S68). This threshold is set similarly to that in the second embodiment.

Subsequently, the region of interest setting unit 34 determines whether there are matching regions equal to or less than a threshold in a predetermined number of ultrasound images or more (step S69). When determination reveals that matching regions equal to or less than the threshold are in the predetermined number of ultrasound images or more (Yes at step S69), the region of interest setting unit 34 sets the corresponding regions as the second ROI (step S70). Alternatively, when matching regions equal to or less than the threshold are not in the predetermined number of ultrasound images or more (No at step S69), the ultrasound observation device 6 finishes the series of processes.

After step S70, the average image generation unit 611 generates data on the average image and the elastic image generation unit 362 generates data on the elastic image of the second ROI to output (step S71). The generated data on the average image and the elastic image of the second ROI are output to the display device 4 under the control of the display control unit 371. The ultrasound observation device 6 then finishes the series of processes. The process of the average image generation unit 611 may also be performed in parallel with the processes from step S68 to step S70 described above.

The following describes a case when the input unit 33 does not receive the average instruction signal (No at step S67) at step S67. In this case, the region of interest setting unit 34 extracts a region in which the displacement amount is equal to or less than a threshold within the first ROI (step S72). This threshold is also the same as the threshold at step S6 described in the first embodiment.

Processes from step S73 to step S75 performed after step S72 respectively correspond to the processes from step S51 to step S53 described in the second embodiment. After step S75, the ultrasound observation device 6 finishes the series of processes.

The present modification 2-1 described above can accurately set the relatively stiff region as the second ROI, because the displacement amount at each observation point of each of the ultrasound images stored in the displacement amount storage unit is referred to, and when matching regions the displacement amount of which is smaller than the threshold are in the predetermined number of ultrasound images or more in the ultrasound images, the regions are set as the second ROI.

OTHER EMBODIMENTS

Figure 10:
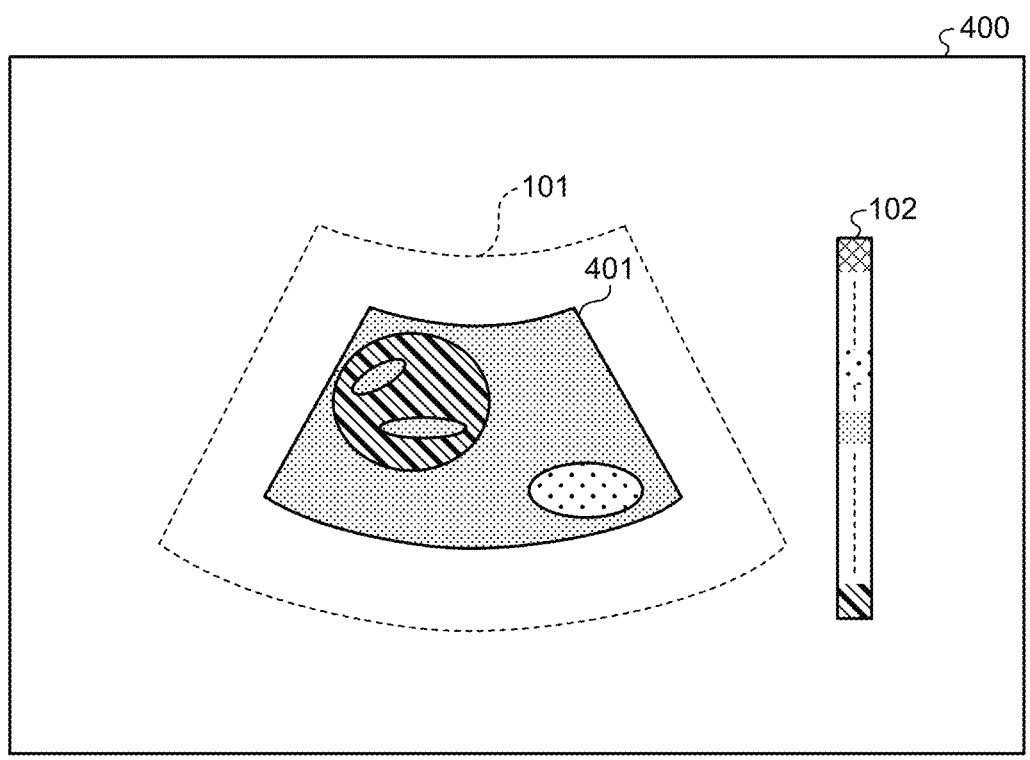
FIG. 10 is a diagram illustrating a display example of an elastic image of a second region of interest on the display device in the other embodiment of the disclosure.

The modes for carrying out the disclosure have been described. However, the disclosure is not only limited to the first and second embodiments described above. For example, the second ROI may be set by a predetermined shape. FIG. 10 is a diagram illustrating a display example of an elastic image of the second ROI having a predetermined shape on the display device 4. In an elastic image 400 illustrated in FIG. 10, the shape of a second ROI 401 is substantially similar to that of the first ROI 101, and the position of gravity is the same as that of the first ROI 101.

For example, an ultrasound miniature probe without an optical system and that has a small diameter may also be applied as an ultrasound probe. In general, the ultrasound miniature probe is inserted into biliary tract, bile duct, pancreatic duct, trachea, bronchus, urethra, and urinary duct, and is used for observing the surrounding organs (pancreas, lung, prostate, urinary bladder, lymph node, and the like). The ultrasound probe may also be an extracorporeal ultrasound probe that emits ultrasound from the body surface of the subject. In general, the extracorporeal ultrasound probe is used for observing abdominal organs (liver, gallbladder, and urinary bladder), breasts (particularly mammary gland), thyroid gland, and the like.

The disclosure enables a user to easily perform both observations on screening and careful examination in ultrasound elastography without taking trouble.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation device comprising a controller, wherein the controller is configured to:
    generate data on an ultrasound image based on an ultrasound signal;
    automatically set a second region of interest that is relatively stiff in a first region of interest preset within the ultrasound image; and
    generate data on first and second elastic images each having a display mode according to stiffness of the corresponding first and second regions of interest, wherein
the controller is further configured to:
    calculate a displacement amount of an observation target in the first region of interest, compare the displacement amount of each observation point in the first region of interest with a predetermined threshold, and when a region in which the displacement at each observation point in the first region of interest amount is smaller than the threshold is spatially continued for a predetermined number of times or more, and the region that is continuous is continued for a predetermined period time, set the region as the second region of interest.

2. The ultrasound observation device according to claim 1, wherein the controller is further configured to:

generate data on the first and second elastic images each having a display mode according to the displacement amount in the corresponding first and second regions of interest as the display mode according to the stiffness of the corresponding first and second regions of interest.

3. The ultrasound observation device according to claim 1, wherein the controller is further configured to cause a display to display an elastic image of a region excluding the second region of interest from the first region of interest and an elastic image of the second region of interest, in a single image having an identifiable display mode by using a color scale corresponding to each of the first region of interest and the second region of interest.

4. The ultrasound observation device according to claim 1, wherein the display mode according to the stiffness of the first region of interest is a color or pattern, and the display mode according to the stiffness of the second region of interest is a color or pattern.

5. The ultrasound observation device according to claim 1, wherein the first elastic image is an image that represents a distribution of stiffness within the first region of interest, and the second elastic image is an image that represents a distribution of stiffness within the second region of interest.

* * * * *